| United States Patent [19] | [11] Patent Number: 4,801,331 |
| Murase | [45] Date of Patent: Jan. 31, 1989 |

[54] NAIL LACQUER REMOVER COMPOSITION

[75] Inventor: Akira Murase, Nagoya, Japan

[73] Assignee: Suhama Chemical Co., Ltd., Nagoya, Japan

[21] Appl. No.: 157,027

[22] Filed: Feb. 18, 1988

[51] Int. Cl.$^4$ .............................................. C09G 1/00
[52] U.S. Cl. .......................................... 106/5; 106/3; 106/176; 106/311; 252/364; 424/61
[58] Field of Search ....................... 106/3, 5, 176, 311; 424/61; 252/130, 364

[56] References Cited

U.S. PATENT DOCUMENTS 4,640,713  2/1987  Harris ....................................... 106/3
4,712,571  12/1987  Remz et al. ............................... 106/5

Primary Examiner—Paul Lieberman
Assistant Examiner—Willie J. Thompson
Attorney, Agent, or Firm—Armstrong, Nikaido, Marmelstein & Kubovcik

[57] ABSTRACT

A nail lacquer remover of the transparent gel type, consisting essentially of: (1) 30–65% by weight of a carbonate selected from the group consisting of ethylene carbonate, propylene carbonate, butylene carbonate and glycerine carbonate; (2) 10–50% by weight of 1,3-dimethyl-2-imidazolidinone; (3) 0.2–20% by weight of hydroxypropyl cellulose; and (4) 13–40% by weight of water. The nail lacquer remover has low flammability, and does not cause drying and cracking of nails.

6 Claims, No Drawings

NAIL LACQUER REMOVER COMPOSITION

BACKGROUND OF THE INVENTION

This invention pertains to a nail lacquer remover composition.

In general, nail enamels contain nitrocellulose as their main component. Conventional nail lacquer removers which are used for removing coatings of the nail lacquer from the nails are usually based on solvents such as acetone and ethyl acetate which dissolve the nitrocellulose. However, these solvent-based conventional nail lacquer removers which contain a large amount of solvent have the following drawbacks:

(1) The solvents, such as ketones and esters, have a low boiling point and are very flammable. Therefore, there is a significant danger of fire or explosion associated with solvent-based nail lacquer removers, particularly during their production but also during their use.

(2) These solvents tend to extract oils and moisture from the nails, causing cracks in the nails and making them coarser in appearance.

(3) Solvent-based nail lacquer removers cause certain fabrics of clothing to become decolorized when the nail lacquer removers are inadvertently spilled on the clothing.

In order to avoid the above drawbacks, it has been known to add oils or esters (other than the esters serving as solvents) to the nail lacquer remover composition. Another method has been to make a cream-type nail lacquer remover by adding a metal soap and oil. However, in any of these methods, the resulting composition still contains ethyl alcohol, methyl alcohol, ethyl acetate or acetone. Therefore, these conventional nail lacquer removers, which cause less damage to nails, remain nevertheless dangerous because of their high flammability and their risk of explosion.

SUMMARY OF THE INVENTION

An object of this invention is to provide a nail lacquer remover which is not flammable and does not cause damage to nails. The nail lacquer composition which achieves these goals is a nail lacquer remover of the transparent gel type, consisting essentially of: (1) a carbonate selected from the group consisting of ethylene carbonate, propylene carbonate, butylene carbonate and glycerine carbonate; (2) 1,3-dimethyl-2imidazolidinone; (3) hydroxypropyl cellulose, and (4) water.

DESCRIPTION OF THE INVENTION

The nail lacquer remover of this invention contains as two key ingredients a carbonate selected from the group consisting of ethylene carbonate, propylene carbonate, butylene carbonate and glycerine carbonate; and 1,3-dimethyl-2-imidazolidinone (DMI). The carbonate and DMI readily dissolve nitrocellulose and are very safe materials due to their high boiling points and their very low flammabilities. The amounts of carbonate and 1,3-dimethyl-2-imidazolidinone in the nail lacquer remover are in the range of 30–65% and 10–50% by weight, respectively.

The nail lacquer remover of this invention also contains 13–40% by weight of water (preferably 15–40%), and 0.2–20% by weight (preferrably 0.2–10%) of hydroxypropyl cellulose.

The amount of DMI in the nail lacquer remover of this invention is in the range of 10–50% by weight, based on the weight of the overall composition. Commercially available DMI, such as DMI from Kawaken Fine Chemicals Co., Ltd., may be used in the nail lacquer remover composition of this invention.

The DMI is essential for dissolving the nitrocellulose which is a main constituent of nail lacquers, and also for maintaining the mixture of carbonate, water and hydroxypropyl cellulose in a viscous, transparent gel-like condition. In the absence of DMI, the carbonate does not mix readily with water and the hydroxypropyl cellulose. Therefore, the amount of water must be limited to 12% by weight or less in order for a homogeneous mixture of carbonate, water and hydroxypropyl cellulose to be obtained in the absence of DMI. However, such a composition which contains only 12% of water has a very low viscosity, and is very inconvenient to use due to its tendency to drip during application to the nails.

The inventor has discovered that the addition of DMI into a mixture of the carbonate, water and hydroxypropyl cellulose makes it possible to increase the water content of the composition without causing it to become non-homogeneous. The resulting composition has an increased viscosity so that the nail lacquer remover remains on the nails for a longer period of time without dripping. The addition of DMI in the range of 10–50% by weight makes possible the incorporation of water in the range of 13–40% by weight into the nail lacquer remover composition.

Hydroxypropyl cellulose, which forms a gel when dissolved in water or water soluble solvents, is essential in the composition of this invention for increasing the viscosity of the mixture of carbonate, water and DMI. The following three types of hydroxypropyl cellulose are available commercially: low viscosity (L), medium viscosity (M) and high viscosity (H). It is preferrable to use each type of hydroxypropyl cellulose in the following respective ranges, which give approximately the same degree of viscosity.

(L) 1–10% by weight
(M) 0.5–5% by weight
(H) 0.2–2% by weight

The nail lacquer remover composition of this invention may contain additives such as anionic or nonionic surfactants. The carbonates used in this invention already have a high degree of wettability, and surfactants are usually not required in the composition of this invention. However, surfactants may be added to the extent that they do not reduce the effectiveness of the nail lacquer remover.

Other additives include perfumes, coloring, vegetal or animal oils, polyethylene glycol or other humectants.

In mixing the components of the nail lacquer remover of this invention, it is generally advantageous to heat the components up to 40° C. in order to facilitate the preparation of a homogeneous mixture.

The nail lacquer remover of this invention is remarkable in that its effectiveness in removing a coating of nitrocellulose is the same as the effectiveness of a nail lacquer remover containing less water and more carbonate. In other words, the addition of a large amount of water in the range of 13–40% does not reduce the effectiveness of the composition in removing nail lacquer. In addition, the condition of the nails is not affected by the use of the nail lacquer remover of this invention.

The following examples are illustrative of the invention. However, the invention is not limited to the examples described below.

EXAMPLES

Nail lacquer remover compositions were prepared from the components shown in the following table, wherein all the proportions are expressed in % by weight based on the weight of the overall composition.

| Example | 1 | 2 | 3 | 4 | 5 | 6 |
|---|---|---|---|---|---|---|
| Propylene carbonate | 50.0 | 48.0 | 50.0 | 30.0 | 50.0 | 40.0 |
| DMI | 30.0 | 35.0 | 20.0 | 50.0 | 30.0 | 10.0 |
| Hydroxypropyl cellulose | 2.0 | 1.0 | 2.0 | 2.0 | 2.0 | 1.0 |
| (type) | (M) | (H) | (M) | (M) | (M) | (M) |
| Water | 17.8 | 15.8 | 18.0 | 18.0 | 18.0 | 39.0 |
| Ethanol | — | — | 10.0 | — | — | 10.0 |
| Perfume | 0.2 | 0.2 | — | — | — | — |

The ingredients listed in the above table were mixed in the following manner. The hydroxypropyl cellulose, DMI, ethanol, water and perfume were added successively in that order to propylene carbonate. The resulting mixture was stirred at 40° C. until a homogeneous, viscous and transparent gel was obtained.

The obtained nail lacquer remover in each example was applied to a cotton pad, and the pad was then used to wipe a dried and cured coating of nail lacquer from nails. In each example, the nail lacquer was entirely removed by this process, and the shade and lustre of the nails after the removal of the lacquer were the same as the shade and lustre observed in nails to which no nail lacquer had been applied and then subsequently removed.

I claim:

1. A nail lacquer recover composition, consisting essentially of:
   (a) 30–65% by weight of a carbonate selected from the group consisting of ethylene carbonate, propylene carbonate, butylene carbonate and glycerine carbonate;
   (b) 10–50% by weight of 1,3-dimethyl-2-imidazolidinone;
   (c) 0.2–20% by weight of hydroxypropyl cellulose; and
   (d) 13–40% by weight of water.

2. The nail lacquer remover composition of claim 1, wherein the amount of hydroxypropyl cellulose is 0.2–10% by weight.

3. The nail lacquer remover composition of claim 1, wherein the amount of water is 15–40% by weight.

4. The nail lacquer remover composition of claim 1, wherein the carbonate is propylene carbonate.

5. The nail lacquer remover composition of claim 2, wherein the carbonate is propylene carbonate.

6. The nail lacquer remover composition of claim 3, wherein the carbonate is propylene carbonate.

* * * * *